United States Patent [19]

Newman

[11] Patent Number: 5,616,748
[45] Date of Patent: Apr. 1, 1997

[54] PROCESS FOR PREPARATION OF REDUCED METAL TITANIUM COMPLEXES

[75] Inventor: Thomas H. Newman, Midland, Mich.

[73] Assignee: The Dow Chemical Company, Midland, Mich.

[21] Appl. No.: 429,392

[22] Filed: Apr. 25, 1995

Related U.S. Application Data

[63] Continuation-in-part of Ser. No. 181,940, Jan. 18, 1994, abandoned.

[51] Int. Cl.$^6$ .............................. C07F 17/00; C07F 7/00; C07F 9/02
[52] U.S. Cl. ................................ 556/11; 556/12; 556/20; 556/52; 556/53; 556/54; 556/56; 526/943; 502/155; 502/158
[58] Field of Search .................................. 556/11, 12, 20, 556/52, 53, 54, 56; 526/943; 502/155, 158

[56] References Cited

U.S. PATENT DOCUMENTS 5,264,590  11/1993  Strickler .................................. 549/208

OTHER PUBLICATIONS

J. Skupinska and W. Skupinski: "ESR Investigation of Ti$^{+3}$ Compounds Supported on Inorganic Gels", React. Kinet. Catal. Lett., vol. 16, No. 2–3, 297–300; (1981).

Chemical Abstracts, vol. 95, No. 14, 5 Oct. 1981, Columbus, Ohio, Abstract No. 121521r, Skupinska, J. et al. "ESR Investigation of Titanium (+3) Compounds Supported on Inorganic Gels", p. 400.

J. Am. Chem. Soc., 3,581 (1961).

Gmelin Handbuch der Anorganischen Chemie, Springer-Verlag, p. 134, (1977).

Primary Examiner—Porfirio Nazario-Gonzalez

[57] ABSTRACT

A process for preparing titanium or zirconium hydrocarbyloxide complexes in a reduced oxidation state comprising contacting the corresponding complex in an elevated oxidation state with lithium alkyl reducing agent and recovering the resulting product.

6 Claims, No Drawings

PROCESS FOR PREPARATION OF REDUCED METAL TITANIUM COMPLEXES

CROSS REFERENCE TO RELATED APPLICATION

This is a continuation-in-part of U.S. application Ser. No. 08/181,940, filed Jan. 18, 1994, now abandoned, the teachings of which are incorporated by reference herein.

BACKGROUND OF THE INVENTION

The present invention relates to a process for preparing titanium or zirconium metal complexes in a reduced oxidation state. More particularly, the present process relates to a process for preparing such metal complexes containing hydrocarbyloxy substituents in a high yield, facile manner. The resulting metal complexes are used for polymerizing α-olefins including ethylene as well as vinylidene aromatic monomers, such as styrene. Generally the catalysts are activated for use by an activating cocatalyst such as an alkylaluminoxane or a cation forming compound. Such polymers may be usefully employed in the preparation of solid objects and articles such as a moldings, films, sheets and foamed objects by molding, casting or the like process.

In *J. Am. Chem. Soc.*, 3, 581 (1961) the preparation of cyclopentadienyltitanium dichloride by the reaction of diisobutyl aluminum chloride with biscyclopentadienyl titanium dichloride is disclosed. In *Gmelin Handbuch der Anorganischen Chemie*, Springer-Verlag, p 134, (1977), cyclopentadienyl titanium dihalides were stated to be prepared by reduction of the corresponding trihalide complexes using powdered zinc reducing agent in dry, oxygen free tetrahydrofuran.

SUMMARY OF THE INVENTION

According to the present invention there is now provided a process for preparing titanium or zirconium metal complexes corresponding to the formula:

$$Cp_mMX_nX'_p$$

wherein:
Cp is a single $\eta^5$-cyclopentadienyl or $\eta^5$-substituted cyclopentadienyl group, the substituted cyclopentadienyl group being optionally also bonded to M through a substituent X as described hereinafter;

M is titanium or zirconium in the $+3$ oxidation state;

X independently each occurrence is an inert anionic ligand of up to 20 nonhydrogen atoms selected from the group consisting of hydrocarbyl, silyl, $NR_2$, $PR_2$, OR, SR, $BR_2$, and combinations thereof, wherein R is $C_{1-10}$ hydrocarbyl, and optionally one X and Cp are joined together forming the divalent ligand, —CpX—;

X' is an inert, neutral donor ligand;

m is 0, 1 or 2;

n is an integer greater than or equal to 1;

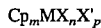 is independently 0 or 1; and the sum of m and n is equal to 3, the steps of the process comprising contacting a metal complex corresponding to the formula:

$$Cp_mM'X''_{n+1}X'_p$$

wherein:
Cp, X', m, n and p are as previously defined;

M' is titanium or zirconium in the $+4$ oxidation state;

X" independently each occurrence is X, with the proviso that in at least one occurrence X" is OR, wherein X and R are as previously defined;

with a lithium alkyl reducing agent and recovering the resulting product.

DETAILED DESCRIPTION OF THE INVENTION

All reference to the Periodic Table of the Elements herein shall refer to the Periodic Table of the Elements, published and copyrighted by CRC Press, Inc., 1989. Also, any reference to a Group or Series shall be to the Group or Series as reflected in this Periodic Table of the Elements, utilizing the IUPAC system for numbering groups.

As used herein, the term "syndiotactic" refers to polymers having a stereoregular structure of greater than 50 percent syndiotactic of a racemic triad as determined by $^{13}C$ nuclear magnetic resonance spectroscopy. Such polymers may be usefully employed in the preparation of articles and objects (e.g., via compression molding, injection molding or other suitable technique) having an extremely high resistance to deformation due to the effects of temperature.

Preferably where X and R are hydrocarbyl the same are σ-bonded groups. Illustrative but nonlimiting examples of X include alkyl, aryl, cycloalkyl, aralkyl, alkaryl, alkoxide, aralkoxide, $SiR^*_3$, —$SiR^*_2NR^*$—, —$SiR^*_2O$—, —$SiR^*_2PR^*$—, —$CR^*_2NR^*$—, —$CR^*_2CR^*_2NR^*$—, and —$CR^*_2CR^*_2O$—, wherein $R^*$ is hydrogen or R, and R is as previously defined.

Illustrative but nonlimiting examples of X' include ROR, RSR, $NR_3$, $PR_3$, and $C_{2-20}$ olefins or diolefins, wherein R is as previously defined. Such donor ligands are able to form shared electron bonds but not a formal covalent bond with the metal.

Monocyclopentadienyl and substituted monocyclopentadienyl groups for use according to the present invention are more specifically depicted by the formula:

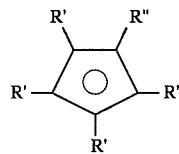

wherein:
R' each occurrence is independently selected from the group consisting of hydrogen, halogen, R, N—$R_2$, P—$R_2$; OR; SR or $BR_2$, wherein R is as previously defined, or one or two pairs of adjacent R' hydrocarbyl groups are joined together forming a fused ring system.

R" individually may be R' or a divalent X group (or X" group depending on whether the reactant or product complex is being referred to) that is also covalently bonded to M.

Preferably, R' is alkyl or haloalkyl of up to 6 carbons. Most highly preferably Cp is cyclopentadienyl or pentamethylcyclopentadienyl.

Illustrative, but not limiting examples of metal complexes which may be used in the preparation of the compounds of this invention are derivatives of titanium or zirconium. Titanium is the preferred metal. In a highly preferred process the complex is formed by reaction of cyclopentadienyl titanium $C_{1-4}$ trialkoxides or pentamethyltitanium $C_{1-4}$ trialkoxides with the reducing agent. That is, Cp in the final product is η⁵-cyclopentadienyl or η⁵-pentamethylcyclopentadienyl, m is one, M is titanium, n is two, p is zero, X each occurrence is OR, and R is $C_{1-4}$ alkyl.

Suitable lithium alkyl reducing agents especially include $C_{1-4}$ alkyl lithium compounds with n-butyl lithium, sec-butyl lithium and t-butyl lithium being preferred, A most highly preferred lithium alkyl reducing agent is t-butyl lithium. The amount of lithium alkyl compound used preferably varies from 0.9 to 2.0 moles per mole of starting complex, and most preferably is from 1.0 to 1.5 moles per mole of starting complex.

Recovery of the resulting complex is accomplished according to any known technique, usually by devolatilization, extraction or precipitation upon addition of a poor solvent. Preferably a quenching agent such as a $C_{1-4}$ trialkylchlorosilane, especially trimethylchlorosilane is added to the reaction mixture to react with unreacted lithium alkyl reducing agent or lithium alkoxide by-products. The amount of quenching agent used preferably varies from 0.9 to 2.0 moles per mole of starting complex, and most preferably is from 1.0 to 1.5 moles per mole of starting complex. The species formed upon addition of the quenching agent are generally volatile and may be removed from the solution by heating. The desired metal complexes are then removed by extraction in a hydrocarbon solvent such as hexane or a mixture of alkanes.

The complexes can be prepared in a suitable solvent at a temperature within the range from about −100° C. to about 300° C. The reactants and products are generally sensitive to both moisture and oxygen and should be handled and transferred in an inert atmosphere such as nitrogen, argon or helium. Suitable solvents or diluents for the complex preparation include any of the solvents known in the prior art including, but not necessarily limited to, straight and branched-chain hydrocarbons such as $C_{6-12}$ alkanes (hexane, heptane, octane and the like); $C_{6-12}$ cyclic and alicyclic hydrocarbons such as cyclohexane, cycloheptane, methylcyclohexane, methylcycloheptane and the like; $C_{6-12}$ aromatic and alkyl-substituted aromatic compounds such as benzene, toluene, xylene, decalin, and the like; inert aliphatic ethers, such as tetrahydrofuran, dimethyl ether, diethyl ether, and the like; and mixtures of the foregoing.

The resulting reduced metal complexes may exist in dimeric form or as coordinated adducts with neutral Lewis bases. The complexes are used in polymerization reactions according to well known Ziegler-Natta reaction conditions. Typical polymerization conditions include slurry, bulk or suspension polymerizations using temperatures of from 0°C. to 160°C. Typical reaction times are from one minute to 100 hours, preferably from 1 to 10 hours. An inert diluent or solvent may be used if desired. Examples of suitable diluents or solvents include $C_{6-20}$ aliphatic, cycloaliphatic, aromatic and halogenated aliphatic or aromatic hydrocarbons, as well as mixtures thereof. Preferred diluents comprise the $C_{6-10}$ alkanes, toluene and mixtures thereof. A particularly desirable diluent for the polymerization is iso-octene, iso-nonane or blends thereof such as Isopar-E®, available from Exxon Chemical Company. Suitable amounts of solvent are employed to provide a monomer concentration from 5 percent to 100 percent by weight.

As in other similar polymerizations, it is highly desirable that the monomers and solvents employed be of sufficiently high purity that catalyst deactivation does not occur. Any suitable technique for monomer purification such as devolatilization at reduced pressures, contacting with molecular sieves or high surface area alumina, deaeration, etc. may be employed.

Having described the invention, the following examples are provided as further illustrative and are not to be construed as limiting. Unless stated to the contrary, all parts and percentages are based on weight.

EXAMPLE 1

All reactions and manipulations were carried out under inert atmosphere in a dry box. Hexane solvent was purified by degassing, sparging with nitrogen and passing through activated alumina prior to use.

A 100 mL Schlenk flask was charged with 1.05 g (3.8 mmol) of pentamethylcyclopentadienyl titanium trimethoxide (Cp*Ti(OCH₃)₃) and 35 mL of tetrahydrofuran (THF). The flask was placed in a dry ice/isopropanol slush bath (−78°C.) 2.4 mL of a 1.7 M THF solution of t-butyllithium (4 mmol) was added by syringe. The resulting solution was stirred for one hour. Via a cannula, a solution of 0.5 g (4.6 mmol) of trimethylchlorosilane in 15 mL of THF was added dropwise with stirring. Over a 14 hour period, the resulting solution was allowed to slowly warm to room temperature with stirring. The volatiles were removed under reduced pressure. The resulting solid was extracted with hexane, the solution was filtered and the product recrystallized at −10°C. The product was a red crystalline solid, identified by 1H NMR and X-ray crystal structure analysis as the dimeric form of pentamethylcyclopentadienyl titanium dimethoxide.

Polymerization

A Catalyst solution was prepared in a volumetric flask using toluene solvent. The required amount of pentamethylcyclopentadienyltitanium dimethoxide (Cp*Ti(OCH₃)₂) was weighed and added to the flask and toluene added to form a 0.01 Molar solution.

Polymerizations were carried out in a septum capped, crimp sealed ampoule. The ampoule was charged with 10 ml of styrene and 75 µl of a 1M solution polymethylaluminoxane (PMA) cocatalyst in toluene. The catalyst solution (37µl) was added and the ampoule was then sealed and equilibrated at 70° C. in a water bath. The polymerization was quenched by the addition of methanol after one hour polymerization time. The polymer sample was isolated and dried in order to determine the percent conversion. Percent conversion was 63 percent. The polymer had a melting point in excess of 260° C. consistent with a syndiotacticity of greater than 50 percent based on a racemic triad.

What is claimed is:

1. A process for preparing titanium or zirconium metal complexes corresponding to the formula:

$$Cp_mMX_nX'_p$$

wherein:

Cp is a single η⁵-cyclopentadienyl or η⁵-substituted cyclopentadienyl group, the substituted cyclopentadienyl group being optionally also bonded to M through a substituent X;

M is titanium or zirconium in the +3 oxidation state;

X independently each occurrence is an inert anionic ligand of up to 20 nonhydrogen atoms selected from the group consisting of hydrocarbyl, silyl, NR₂, PR₂, OR, SR, BR₂, and combinations thereof, wherein R is $C_{1-10}$ hydrocarbyl, and optionally one X and Cp are joined together forming the divalent ligand, —CpX—;

X' is an inert, neutral donor ligand;

m is 0, 1 or 2;

n is an integer greater than or equal to 1;

p is independently 0 or 1; and the sum of m and n is equal to 3, the steps of the process comprising contacting a metal complex corresponding to the formula:

$$Cp_mM'X''_{n+1}X'_p$$

wherein:

Cp, X', m, n and p are as previously defined;

M' is titanium or zirconium in the $^+4$ oxidation state;

X" independently each occurrence is X with the proviso that in at least one occurrence X" is OR, wherein X and R are as previously defined;

with a lithium alkyl reducing agent and recovering the resulting product.

2. The process according to claim 1 wherein M is titanium.

3. The process according to claim 1 wherein Cp is cyclopentadienyl or pentamethylcyclopentadienyl.

4. The process according to claim 1 wherein the complex is recovered by quenching with a $C_{1-4}$ trialkylchlorosilane, devolatilizing the resulting solution and extracting the desired complex.

5. The process according to claim 3 wherein the $C_{1-4}$ trialkylchlorosilane is trimethylchlorosilane.

6. The process according to claim 1 wherein the alkyllithium reducing agent is tert-butyl lithium.

* * * * *